(12) United States Patent
Brown et al.

(10) Patent No.: US 8,476,028 B2
(45) Date of Patent: Jul. 2, 2013

(54) SEPSIS TEST

(75) Inventors: Kenneth Alun Brown, Middlesex (GB); Sion Marc Lewis, Buckinghamshire (GB)

(73) Assignee: King's College London, London (GB)

( * ) Notice: Subject to any disclaimer, the term of this patent is extended or adjusted under 35 U.S.C. 154(b) by 0 days.

(21) Appl. No.: 13/342,669

(22) Filed: Jan. 3, 2012

(65) Prior Publication Data

US 2012/0315653 A1  Dec. 13, 2012

Related U.S. Application Data

(63) Continuation of application No. 12/162,820, filed as application No. PCT/GB2007/000325 on Jan. 31, 2007, now abandoned.

(30) Foreign Application Priority Data

Jan. 31, 2006 (GB) .................................. 0601959.0

(51) Int. Cl.
G01N 33/00 (2006.01)
G01N 33/53 (2006.01)
G01N 33/554 (2006.01)
G01N 33/569 (2006.01)

(52) U.S. Cl.
USPC ............ 435/7.1; 435/7.2; 435/7.24; 435/7.32

(58) Field of Classification Search
None
See application file for complete search history.

(56) References Cited

U.S. PATENT DOCUMENTS

| 5,830,679 | A | 11/1998 | Bianchi et al. |
| 6,835,815 | B2 | 12/2004 | Nunez et al. |
| 2003/0077576 | A1* | 4/2003 | Trial et al. ......................... 435/5 |

FOREIGN PATENT DOCUMENTS

| EP | 1 213 586 | 6/2002 |
| WO | 02/074789 A | 9/2002 |

OTHER PUBLICATIONS

Subrahamanyam et al., "RNA Expression patterns change dramatically in human neutrophils exposed to bacteria" Blood, W.B. Saunders Company, Orlando, FL, US, vol. 97, No. 8, Apr. 15, 2001, pp. 2457-2468, XP002366275.
Al-Numani et al., "Up-regulation of ICAM-1, CD11a/CD18 and CD11c/CD18 on human THP-1 monocytes stimulated by Streptococcus suis serotype 2." Jul. 2003, Clinical and Experimental Immunology, vol. 133, NR. 1, pp. 67-77, XP002437185.
Kang Yuan-Hsu et al., "Effects of endotoxin on expression of VLA integrins by human bronchoalveolar lavage macrophages" 1995, Journal of Leukocyte Biology, vol. 57 NR. 4, pp. 624-634, XP002437186.
Hofman et al., "Increased *Escherichia coli* phagocytosis in neutrophils that have transmigrated across a cultured intestinal epithelium" Feb. 2000, Infection and Immunity, vol. 68, NR. 2, pp. 449-455, XP002437187.
Yang et al. (Nature vol. 395, pp. 284-288, 1998).
Extended European Search Report issued in corresponding European Application No. 10192466.0, dated Mar. 23, 2012.
Moller et al., "Chemokin production and pattern recognition receptor (PRR) expression in whole blood stiulated with pathogen-associated molecular patterns (PAMPs)," Cytokin, Academic Press Ltd., vol. 32, No. 6, pp. 304-315, Dec. 21, 2005.
Nilsen et al, "Lipopolysaccharide and Double-stranded RNA Up-regulate Toll-like Receptor 2 Independently of Myeloid Differentiation Factor 88," Journal of Biological Chemistry, vol. 279, No. 38, pp. 39727-39735, Jan. 1, 2004.
Keller et al., "Macrophage Response to Microbial Pathogens: Modulation of the Expression of Adhesion, CD14, and MHC Class II Molecules by Viruses, Bacteria, Protozoa and Fungi," Scandinavian Journal of Immunology, vol. 42, No. 3, pp. 337-344, Sep. 1, 1995.
Hansen et al., "Inflammatory activation of neutrophils by *Helicobacter pylori*; a mechanism insensitive to pertussis toxin," Clinical & Experimental Immunology, vol. 123, No. 1, pp. 73-80, Jan. 1, 2001.
Tsokos et al, "Post-mortem markera of sepsis: an immunohistochemical study using VLA-4 (CD49d/CD29) and ICAM-1 (CD54) for the detection of sepsis-induced lung injury," International Journal of Legal Medicine, vol. 114, No. 4-5, pp. 291-294, Apr. 10, 2001.
Brandl et al., "TLR-4 surface dispay on human monocytes is increased in septic patients," Eur. J. Med. Res., vol. 10, pp. 319, Aug. 17, 2005.
Great Britain Search Report issued in related Great Britain Application No. GB0601959.0, dated Jan. 31, 2007.
Wagner et al, "Expression patterns of the Lipopolysaccharide Receptor CD14, and the FCγ Receptors CD16 and CD64 on Polymorphonuclear Neutrophils: Data from Patients with Severe Bacterial Infections and Lipopolysaccharide-Exposed Cells," Shock, vol. 19, pp. 5-12, 2003.
Takeshita et al., "Increased levels of circulating soluble OD14 in Kawasaki disease," Clin. Exp. Immunol. 119:376-381, 2000.
Harter et al., "Increased Expression of Toll-Like Receptor-2 and -4 on Leukocytes from Patients with Sepsis," Shock, vol. 22, No. 5, pp. 403-409, 2004.
Lim et al, "Cell adhesion-related gene expression by *Helicobacter pylori* in gastric AGS cells," The International Journal of Biochemistry & Cell Biology, vol. 35, pp. 1284-1296, 2003.

* cited by examiner

*Primary Examiner* — Albert Navarro
(74) *Attorney, Agent, or Firm* — Banner & Witcoff, Ltd

(57) ABSTRACT

There is provided a method for determining whether a subject has a bacterial infection comprising: identifying an abnormal expression of one or more of CD49e, CD 14, CD11c, CD49f, and CD29 on leucocytes in a sample obtained from the subject; wherein an abnormal expression of CD49e, CD 14, CD11c, CD49f or CD29 is indicative of the subject having a bacterial infection.

7 Claims, 3 Drawing Sheets

SEPSIS TEST

Figure 1:
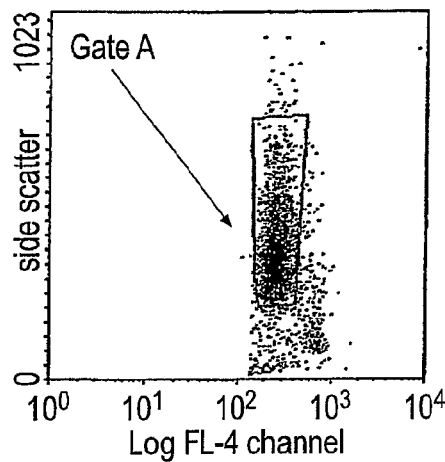

The invention relates to a test for determining whether a subject has a bacterial infection, especially bacterial sepsis.

Organ failure arising from sepsis is one of the major causes of patient mortality within the Intensive Care Unit (ICU). Despite the technological support of organ function, a mortality of approximately 30% is reported in patients with sepsis and should multiple organ failure develop then the mortality may exceed 80%. Current guidelines recommend early antibiotic treatment in response to definitive evidence that bacterial infection is the cause of organ failure. Confirmation of bacterial infection in blood and other sites is only available in a proportion of patients and takes at least 24-48 hours. Rapid indirect markers of, bacterial infection include increases in peripheral blood leucocyte counts and in serum levels of acute phase proteins, C-reactive protein and pro-calcitonin. Since these markers are also elevated in ICU patients with systemic inflammation, who have no evidence of bacterial infection, they cannot be used to guide therapy. Thus, definitive information necessary for clinical diagnosis is unavailable at a critical stage of patient management. Consequently, broad spectrum antibiotics are often started early, in the hope that they will arrest patient deterioration. Alternatively, in some situations no antibiotics are prescribed in the first 48 hours in the mistaken belief that the cause of the organ failure is non-bacterial. This may result in a potentially life-threatening delay in starting antibiotics.

Antibiotics are often administered inappropriately for several days to patients in the ICU who do not have bacterial infections, because it is considered unethical to withhold antibiotics if bacterial infection cannot be confidently excluded. The bacteria implicated in ICU-acquired sepsis are endogenous, commensal or environmental. The over use of antibiotics, when unnecessary, is adding to increasingly unpredictable antibiotic resistance. The consequence of this therapeutic approach has been a steady but inexorable rise in antibiotic resistance of hospital-acquired bacteria, as illustrated by methicillin resistant *Staphylococcus aureus* (MRSA) and multi-resistant Gram-negative bacteria such as *Acinetobacter* and *Pseudomonas* species. With new international ICU guidelines recommending that treatment of sepsis patients with broad-spectrum antibiotics be started within a few hours of diagnosis as a standard of care, it seems that antibiotic resistance will increase. Against this background there is a need to develop an assay for the rapid detection of bacterial infections in critically ill patients.

The organ failure associated with sepsis is precipitated by the systemic inflammation that is produced in response to invasive bacteria. The main function of neutrophils is to destroy pathogenic bacteria but evidence is emerging that these cells are also implicated in the initiation of organ dysfunction in patients with sepsis. In recent years the inventors have been addressing the working hypothesis that an untoward interaction of blood neutrophils with endothelium produces organ dysfunction, either by vascular occlusion that leads to hypoxia and tissue hyperperfusion, or by disruption of the endothelium and an increase in vascular permeability. Accordingly, the inventors' studies of neutrophils from patients with sepsis have focused on the expression of adhesion molecules, which are known to promote adhesion to blood vessel walls, and on cellular receptors that contribute to bacterial recognition. During the course of this work the inventors noted that neutrophils expressing seven distinct molecules were more prevalent in the blood of patients with sepsis than in patients with systemic inflammation initiated by non-infective stimuli such as surgery, trauma and pancreatitis and in healthy control subjects (see Tables 1, 2, 3 & 4). These molecules were CD49e, CD14, CD11c, CD49f, CD29; TLR2 and TLR4.

The inventors have developed a rapid and accurate test for assessing whether a subject has a bacterial infection. This test is particularly useful for assessing whether a patient with systemic inflammation has a bacterial infection:

According to the invention, there is provided a method for determining whether a subject has a bacterial infection comprising:

a) identifying an abnormal expression of one or more of CD49e, CD14, CD11c, CD49f, and CD29 on leucocytes in a sample obtained from the subject;

wherein an abnormal expression of CD49e, CD14, CD11c, CD49f or CD29 is indicative of the subject having a bacterial infection.

The method is particularly useful because it may be carried out quickly, within several hours of sample collection, allowing a rapid decision to be taken as to whether to administer antibiotics to the subject.

The terms "sepsis" and "systemic inflammatory response syndrome" (SIRS) are well known in the art and mean a systemic inflammatory response to infection, usually bacterial infection. In its most severe form, sepsis results in organ dysfunction and failure.

The term "bacterial infection" means the presence in a subject of bacteria not normally found in the subject or an increased number or change of location of bacteria normally found in the subject such as endogenous or commensal bacteria. For example, the infection could be due to an invasion of the blood by bacteria normally found in the gut. Alternatively the infection could be due to bacteria not normally found within the body.

The infection may be an infection of Gram positive or Gram negative bacteria. Both terms are well known in the art.

As indicated above, it would be very useful to be able to determine whether organ failure or dysfunction in a patient arises from sepsis caused by a bacterial infection and hence whether to treat the patient with antibiotics.

The subject may be any animal, preferably a mammal. It is more preferred that the subject is a primate, especially a human.

The subject may be showing signs of systemic inflammation, organ dysfunction or failure or may not be exhibiting any such symptoms.

The leucocytes may be any type of leucocytes, but are preferably monocytes or neutrophils. In particular, the leucocytes may be neutrophils.

CD49e & CD49f belong to a family of β1 integrin adhesion molecules. Integrins are heterodimers that consist of different α chains and a common β chain. It is the β chain that defines the family and for the β1 integrins this molecule is known as CD29. There are six members (CD49a/CD29→CD49f/CD29) and their α chains are, in addition to their CD nomenclature, referred to as very late antigen (VLA-1 to VLA-6). Hence, CD49e/CD29 is also known as VLA-5, and CD49f/CD29 is also known as VLA-6. The ligands for the β1 integrins are components of the extracellular matrix and CD49e binds to fibronectin. In general, expression of the β1 integrins is confined to the surface of lymphocytes and monocytes but not resting blood neutrophils. CD11c is a member of the β2 integral family whereas CD14 is a receptor for lipopolysaccharide (LPS).

An abnormal expression of CD49e, CD14, CD49f, CD11c or CD29 means that the expression of the molecule is significantly higher, as assessed by statistical analysis, on some leucocytes or that many leucocytes show a significantly increased expression compared with levels on normal resting blood leucocytes. That is to say, some leucocytes may express an increased number of CD49e, CD14, CD49f, CD11c or CD29 molecules, or an increased number of leucocytes may express CD49e, CD14, CD49f, CD11c or CD29 molecules when compared with normal resting blood leucocytes.

In particular, an abnormal expression of CD49e preferably means that the mean distribution of CD49e positive leucocytes is at least 50% more than the mean distribution of CD49e positive leucocytes in normal resting blood leucocytes. Preferably the mean distribution is increased by at least 75%, more preferably by at least 100%, even more preferably by at least 150% and most preferably by at least 200%.

An abnormal expression of CD14 preferably means that the mean distribution of CD14 positive leucocytes is at least 50% more than the mean distribution of CD14 positive leucocytes in normal resting blood leucocytes. Preferably the mean distribution is increased by at least 75%, more preferably by at least 100%, even more preferably by at least 150% and most preferably by at least 200%.

An abnormal expression of CD49f preferably means that the mean distribution of CD49f positive leucocytes is at least 50% more than the mean distribution of CD49f positive leucocytes in normal resting blood leucocytes. Preferably the mean distribution is increased by at least 75%, more preferably by at least 100%, even more preferably by at least 150% and most preferably by at least 200%.

An abnormal expression of CD11c preferably means that the Mean distribution of CD11c positive leucocytes is at least 50% more than the mean distribution of CD11c positive leucocytes in normal resting blood leucocytes. Preferably the mean distribution is increased by at least 75%, more preferably by at least 100%, even more preferably by at least 150% and most preferably by at least 200%.

An abnormal expression of CD29 preferably, means that the mean distribution of CD29 positive leucocytes is at least 50% more than the mean distribution of CD29 positive leucocytes in normal resting blood leucocytes. Preferably the mean distribution is increased by at least 75%, more preferably by at least 100%, even more preferably by at least 150% and most preferably by at least 200%.

An abnormal expression of CD49e on neutrophils preferably means that the mean distribution of CD49e positive neutrophils in a sample is at least 20% of neutrophils, more preferably at least 25%, even more preferably at least 30%, most preferably at least 40%.

An abnormal expression of CD14 on neutrophils preferably means that the mean distribution of CD14 positive neutrophils in a sample is at least 10% of neutrophils, more preferably at, least 12%, even more preferably at least 15%, most preferably at least 20%.

An abnormal expression of CD49f on neutrophils preferably means that the mean distribution of CD49f positive neutrophils in a sample is at least 20% of neutrophils, more preferably at least 25%, even more preferably at least 30%, most preferably at least 40%.

An abnormal expression of CD11c on neutrophils preferably means that the mean distribution of CD11c positive neutrophils in a sample is at least 40% of neutrophils, more preferably at least 50%, even more preferably at least 60%, most preferably at least 70%.

An abnormal expression of CD29 on neutrophils preferably means that the mean distribution of CD29 positive neutrophils in a sample is at least 40% of neutrophils, more preferably at least 50%, even more preferably at least 60%, most preferably at least 70%.

The sample may be any sample in which leucocytes may be found e.g. bronchioalveolar lavage, urine. Preferably the sample is a blood sample.

It is generally thought by those skilled in the art that in response to bacterial infection, the phenotype of neutrophils changes only when the cells enter an infective lesion. There is no evidence to suggest that neutrophils re-enter the circulation from sites of infection. Those skilled in the art were not interested in examining the surface of neutrophils for signs of bacterial induced changes because it is often very difficult to obtain a sample from the site of the infection. In cases of suspected sepsis, there is a doubt as to whether the patient has a bacterial infection, and, hence, the site of any such infection may be unknown. This reinforced the lack of interest in neutrophils. Surprisingly the inventors have found evidence of bacterial infection on the surface of neutrophils circulating in the blood, thus negating the need to obtain neutrophils from sites of bacterial infection.

The method includes identifying an abnormal expression of any one or more of CD49e, CD14, CD11c, CD49f and CD29. The method preferably comprises identifying an abnormal expression of more than one of these molecules.

The method preferably additionally comprises identifying the abnormal expression of one or both of TLR2 and TLR4 on the leucocytes in the sample, wherein the abnormal expression of one or both of TLR2 and TLR4 is further indication of a bacterial infection.

TLR2 and TLR4 are toll-like receptors. Such receptors are pattern recognition molecules that control innate immune responses to various microbial ligands. These terms are well known in the art.

Both TLR2 and TLR4 may be expressed by leucocytes, especially macrophages at a site of bacterial infection but it is much more likely that one or the other of them is expressed abnormally. TLR2 has been found to be associated with Gram positive bacterial infection, so its abnormal expression on leucocytes is preferably indicative thereof. TLR4 has been found to be associated with Gram negative bacterial infection so its abnormal expression on leucocytes is preferably indicative of such an infection.

Normal blood neutrophils express little TLR2 or TLR4. Generally less than 5% of neutrophils in a sample express TLR2 or TLR4. During the course of their work, the inventors noticed that neutrophils expressing TLR2 were more prevalent in the blood of patients with sepsis who had Gram+ve infections when compared with neutrophils from control subjects (Table 2). The inventors also noted that neutrophils expressing TLR4 and CD14 were increased significantly in the blood of patients with sepsis who had Gram−ve infections when compared with control subjects (Table 2).

An abnormal expression of TLR2 or TLR4 preferably means that the mean distribution of TLR2 or TLR4 positive leucocytes is at least 50% more than the mean distribution of TLR2 or TLR4 positive leucocytes in normal resting blood leucocytes. Preferably the mean distribution is increased by at least 75%, more preferably by at least 100%, even more preferably by at least 150% and most preferably by at least 200%.

Abnormal expression of TLR2 on neutrophils preferably means that the mean distribution of TLR2 positive neutrophils in a sample is at least 7% of neutrophils, more preferably at least 10%, even more preferably at least 15%, most preferably at least 20%.

Abnormal expression of TLR4 on neutrophils preferably means that the mean distribution of TLR4 positive neutrophils in a sample is at least 10% of neutrophils, more preferably at least 12%, even more preferably at least 15%, most preferably at least 20%.

As noted by the inventors, a patient with sepsis may have neutrophils expressing simultaneously an upregulation of both TLR2 and TLR4 suggesting infection with Gram+ve and Gram−ve bacteria at the same time. (Table 3)

The inventors have noted that an increased expression of CD29 is often indicative of a Gram positive bacterial infection. Hence, the method preferably comprises identifying an abnormal expression of CD29 and TLR2.

The abnormal expression of CD49e, CD14, CD11c, CD49f, CD29, TLR2 and/or TLR4 may be identified in any appropriate manner. In particular, monoclonal, polyclonal antibodies or fragments of them for the molecule in question can be used. The antibodies or fragments are generally conjugated to a marker, such as fluorescein isothiocyanate or phycoerythrin so that the presence of the molecule in question may be observed and measured.

As an example, antibodies conjugated to fluoroscein isothiocyanate or phycoerythrin may be used and the presence of the molecule in question identified and quantified using flow cytometry. Any appropriate flow cytometer may be used, such as a Beckman-Coulter® EPICS-MCL™. One skilled in the art would appreciate that this is merely an example method and any appropriate assay for the molecule in question could be used.

Also provided is a kit for testing for a bacterial infection comprising antibodies or antibody fragments to at least one of CD49e, CD14, CD49f, CD29 and CD11c. Preferably the kit additionally comprises antibodies or antibody fragments to at least one of TLR2, and TLR4. Preferably the kit comprises antibodies or antibody fragments to at least two of CD49e, CD14, CD11c, CD49f, CD29, TLR2 and TLR4.

Preferably the kit comprises antibodies or antibody fragments to CD49e, TLR2, TLR4 and CD14.

Preferably the kit additionally comprises antibodies to CD11c, CD49f and CD29.

Preferably the monoclonal antibodies are marked so the presence of the molecule in question may be confirmed and quantified.

Figure 4:
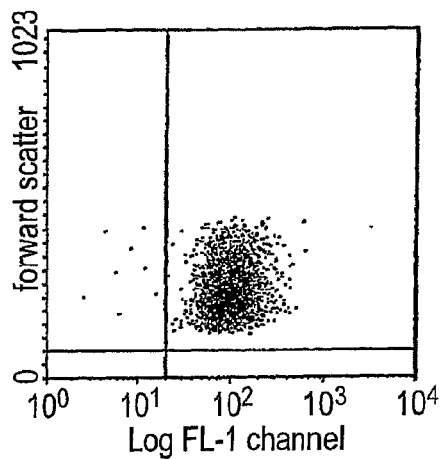
Figure 5:
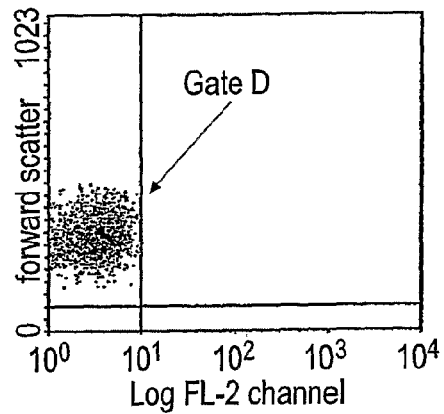
Figure 6:
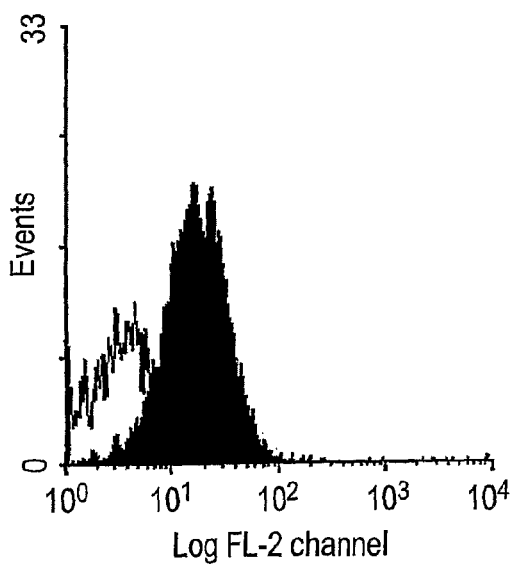

The invention will now be described in detail, by way of example only, with reference to the drawings in which:

FIGS. 1 to 5 show the procedures for configuring flow cytometric analysis equipment to detect the monoclonal antibodies used, and FIG. 6 is a histogram plot of binding of antibodies directed to CD49e on neutrophils from a subject with sepsis (shaded area) and a normal subject (un-shaded area).

Figure 7:
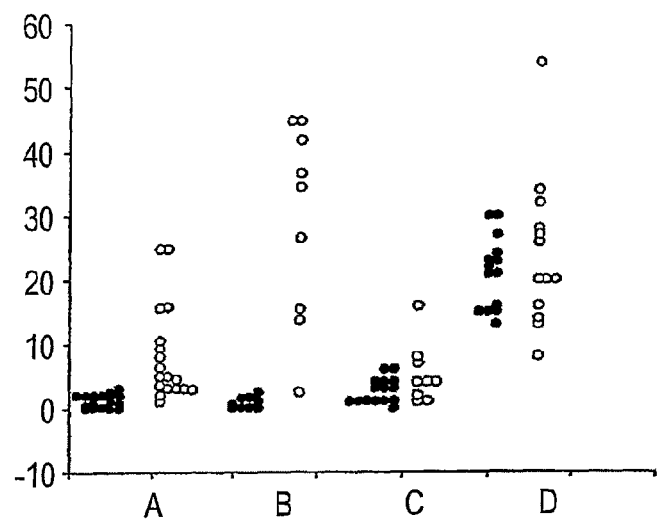

FIG. 7 shows the distribution of neutrophils bearing TLR4 (closed circles) and CD14 (open circles) in normal healthy subjects (A), patients that have undergone cardiac surgery and had no evidence of infection (B), patients with SIRS but with no evidence of infection (C) and SIRS patients with Gram−ve infections (D). The vertical axis describes the percentage of neutrophils stained with anti-TLR4 or anti-CD14 antibodies.

Figure 8:
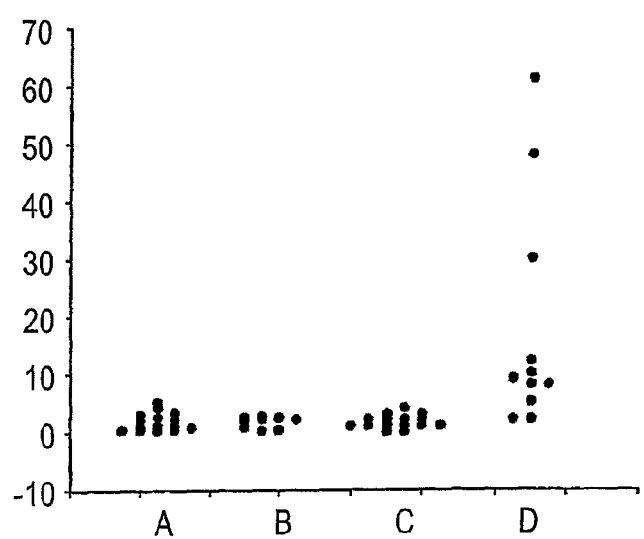

FIG. 8 shows the distribution of neutrophils bearing TLR2 in the three subject groups (normals (A), cardiac (B), SIRS no infection (C)) identified above and also including Gram+ve infections (D). The vertical axis describes the percentage of neutrophils stained with anti-TLR2 antibodies

EXAMPLES

The method involves identification of CD49e, CD14, CD11c, CD49f, CD29, TLR2 and TLR4 on neutrophils by commercially available monoclonal antibodies conjugated with either fluoroscein isothiocyanate (FITC) or phycoerythrin (PE), using the technique of flow cytometric analysis. Suitable antibodies may be obtained from, for example, AbD Serotec (Raleigh, N.C.). The protocol is as follows:

(i) Take 4.5 mL of blood into a pre-cooled (4° C.) EDTA-anticoagulated blood collection tube (Vacutainer™; BD Biosciences®). Then, transfer immediately into a pre-cooled CTAD™-anticoagulated blood collection tube (Vacutainer™; BD Biosciences®).

(ii) Mix 100 μL of anticoagulated whole blood with 100 μL Hank's balanced salt solution (HBSS™, without magnesium, calcium or phenol red; Sigma-Aldrich®) supplemented with 2% Foetal Bovine Serum (Sigma-Aldrich®) and incubate for 20 min at 4° C. Add 2 μl of LDS-751™ (Molecular Probes®), mix by gentle agitation.

(iii) Next, introduce 100 μL of HBSS™ into labelled 12×75 mm LP5 tubes (Falcone®) (cooled to 4° C.) together with 10 μL of the anticoagulated blood mixture and mix gently.

(iv) To each LP5 tube, add 1 μL of the relevant mouse-anti-human monoclonal antibody (mouse IgG1-FITC; Beckman-Coulter®), (TLR2-FITC; Serotec®), (TLR4-PE conjugated; Serotec®), (CD49E-PE; Pharmingen®), (CD66B-FITC, a marker of neutrophils; Beckman-Coulter®). Gently mix the samples and incubate in the dark for 20 min at 4° C.

(v) Wash by adding 200 μL of HBSS to each tube and centrifuge at 300 g for 10 min. Remove the supernatant and resuspend the pellet in 200 μL of MSS. Centrifuge at 300 g for 10 min. Remove supernatant once again and resuspend the remaining pellet in 300 μL Isoton™ sheath fluid (Beckman Coulter®). Samples are now ready for flow cytometric analysis. Analysis must take place within 1 hour.

The inventors currently use a Beckman-Coulter® EPICS-MCL™ with System II™ software for flow cytometric analysis. Prior to sample analysis, the Beckman-Coulter® standard operating procedures (SOP) for quality control assurance must be followed.

FIG. 1 shows FL-4 channel (x-axis), side scatter (y-axis). Set the event 'Discriminator' to FL-4=10. Gate around the most abundant population (Gate A, FIG. 1). The nuclear stain LDS-751 will discriminate between nucleated cells and non-nucleated red blood cells allowing analysis of whole blood without chemical lysis of the red cell population.

Figure 2:
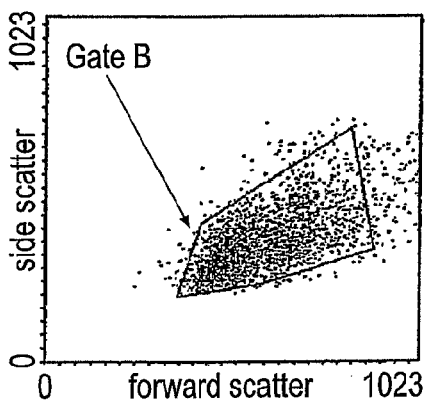

FIG. 2 shows forward scatter (x-axis), side scatter (y-axis). Gate around the abundant neutrophil population (Gate B, FIG. 2), so as to remove potentially contaminating mononuclear cells.

Figure 3:
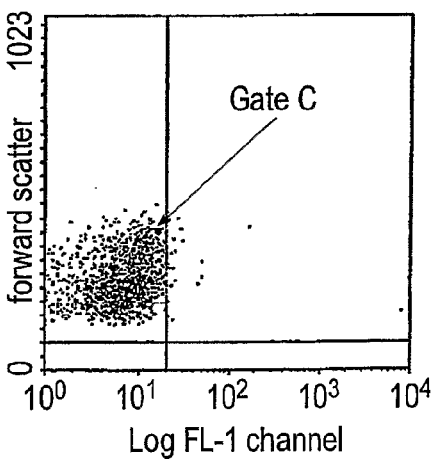

FIG. 3 shows FL-1 channel (x-axis), forward scatter (y-axis). Quadrant created: cursor (intersection on x-axis) positioned to include no more than 1% of gated events in the upper right quadrant following analysis of the IgG1-FITC isotype control sample (Gate C, FIG. 3). The FL-1 channel is now configured for detection of antibodies conjugated with FITC.

FIG. 4 shows FL-1 channel (x-axis), forward scatter (y-axis). Neutrophil staining with anti-CD66B-FITC antibody (positive control). Confirmation of the purity of the neutrophil population is assessed by the percentage of cells within the upper right-hand quadrant when stained with the FITC-conjugated monoclonal antibody directed against CD66B (neutrophil marker).

FIG. 5 shows FL-2 channel (x-axis), forward scatter (y-axis). Quadrant created: cursor (intersection on x-axis) positioned to include no more than 1% of gated events in the upper right quadrant following analysis of the IgG1-PE isotype control sample (Gate D, FIG. 5). The FL-2 channel is now configured for the detection of antibodies conjugated with PE.

FIG. 6 shows FL-2 channel (x-axis), events (y-axis). Test antibody. A representative histogram plot showing staining of PE-conjugated antibody directed towards CD49E on neutrophils from a patient with sepsis (shaded area) and a healthy normal subject (un-shaded area).

The protocol is now configured for single colour analysis of FITC- and PE-conjugated antibody staining of the neutrophil population in whole blood. Samples are passed through the manual-feed, or the automated carousel loader and 5000 gated (neutrophil) events are captured. Data is recorded as the percentage of cells in the positive gate (%) and as the mean fluorescence intensity (MFI) of the gated events.

An advantage of this potential diagnostic test for the identification of bacteria is the generation of results within 2 hours of the provision of a blood sample and that the analysis is performed on a small volume of blood. At present, confirmation of bacterial infection by microbiological examination takes 24-48 hours. This delay leads to excessive antibiotics being administered to patients with sepsis, to the unnecessary use of antibiotics for non-infected critically ill patients and to the spread of antibiotic resistance. An additional asset of the proposed diagnostic test is that flow cytometers could be installed easily within ICU's and that local staff could be trained to operate the equipment very quickly so as to provide a 24 hour service.

Using the techniques described herein, the inventors tested samples from subjects with and without sepsis.

Table 1 shows the high prevalence of CD49e bearing neutrophils in the blood of patients with definite sepsis and Table 2 the incidence of TLR2 and TLR4 positive neutrophils in the circulation of patients with Gram-positive and Gram-negative infections respectively.

TABLE 1

Potential association of blood neutrophil surface molecules with sepsis

| Patient groups | % neutrophils | | | |
|---|---|---|---|---|
| | CD29 | CD49d | CD64 | CD49e |
| 1. Definite sepsis (n = 14) | 57 | 7 | 68 | 57 |
| 2. Probable/possible sepsis (n = 16) | 48 | 4 | 36 | 22 |
| 3. SI - no sepsis (n = 12) | 55 | 7 | 35 | 4 |
| 4. Normals (n = 48) | 48 | 8 | 4 | 6 |

CD64: 1 v 2 (p < 0.01); 1 v 3/4 (p < 0.001); 2/3 v 4 (p < 0.001)
CD49e: 1 v 2 (p < 0.005); 1 v 3/4 (p < 0.001); 2 v 3 (p < 0.05)
n = number of subjects
SI = systemic inflammation Table 2 shows the selective distribution of TLR2, TLR4 and CD14 on blood neutrophils from patients with sepsis, 14 of whom had Gram−ve infections and 9 of whom had Gram+ve infections

| Gram − ve infection % Neutrophils | | | Gram + ve infection % Neutrophils | |
|---|---|---|---|---|
| TLR2 | TLR4 | CD14 | TLR2 | TLR4 |
| 2 | 10 | | 45 | 1 |
| 1 | 32 | | 8 | 0 |
| 3 | 18 | 23 | 10 | 1 |
| 1 | 12 | 74 | 8 | 2 |
| 5 | 54 | 30 | 2 | 12 |
| 2 | 20 | 31 | 5 | 8 |
| 5 | 16 | 16 | 12 | 4 |
| 2 | 26 | 12 | 9 | 32 |
| 3 | 20 | 23 | 30 | 0 |
| 17 | 20 | 63 | | |
| 6 | 34 | 27 | | |
| 2 | 18 | 24 | | |
| 6 | 27 | 21 | | |
| 2 | 27 | 15 | | |
| Mean 4 ± 4 | 24 ± 11 | 30 ± 19 | 14 ± 14 | 7 ± 10 |

| | % Neutrophils | | |
|---|---|---|---|
| | TLR2 | TLR4 | CD14 |
| Normal healthy subjects | 1 ± 1 | 1 ± 1 | 4 ± 3 |
| Patients with SIRS in ICU but no infection | 2 ± 1 | 3 ± 3 | 6 ± 5 |

TLR4 distribution in Gram – ve sepsis
P < 0.001 v non-infected patients
P < 0.001 v healthy controls
TLR2 distribution in Gram + ve sepsis
P < 0.05 v non-infected patients
P < 0.01 v healthy controls
CD14 distribution in Gram – ve patients
P < 0.001 v non-infected patients
P < 0.001 v healthy controls Table 3 shows sequential analysis of blood neutrophils expressing TLR2 and TLR4 in a patient with sepsis.

| | | % Neutrophils | |
|---|---|---|---|
| Day in ICU | Organism Identified | TLR2 | TLR4 |
| 1 | Blood: Gram − ve (*E. Coli* x 1; *Klebsiella* x 1) Sputum: Gram − ve (*Serratia*+++) Hickman line tip: *Serratia*+++ Ascitic fluid: *E. Coli*++ | 2 | 28 |
| 5 | Ascitic fluid: Gram + ve (*Enterococcus*++) | 8 | 2 |
| 8 | No microbiology requested | 13 | 7 |
| 22 | Blood: *Serratia*++ Line tip: *Serratia*++ | 2 | 17 |

In their analysis the inventors found that the mean distribution of CD49e positive neutrophils in healthy controls is 6±6%. A significant increase can be regarded as in excess of the mean of the normal values+2 standard deviations. For CD49e the positive cut-off point is therefore in excess of 18%. On this basis 89% of the patients with definite sepsis had an increase in the percentage of neutrophils expressing CD49e. Using the analysis of receiver operating characteristic (ROC) curves and a cut-off point of 20%, the test provides a sensitivity of 1 and a specificity of 0.9.

Using the ROC analysis the presence of more than 10% TLR4 and 10% CD14 positive neutrophils in the blood gave a positive test for Gram−ve infections. This cut-off point produced a sensitivity of 0.93 and specificity of 0.98. Using a 7% cut-off point for TLR2 bearing neutrophils the test produced a sensitivity of 0.72, and a specificity of 0.98 for Gram+ve infections.

Table 4 shows the distribution of CD11c and CD49f on blood neutrophils obtained from patients with SIRS and sepsis, compared to those with SIRS but not sepsis. It also shows the incidence of CD29 in neutrophils from subjects with a Gram positive infection, compared with those from subjects with a Gram negative infection.

| MOLECULE | SIRS + SEPSIS | SIRS − SEPSIS | NORMALS | MEDIAN VALUES | |
|---|---|---|---|---|---|
| CD11C | 71% (n = 35) | 34% (n = 20) | 37% (n = 45) | p < 0.001 | SIRS + SEPSIS versus SIRS − SEPSIS/ NORMAL |
| CD49F | 19% (n = 24) | 10% (n = 17) | 8% (n = 11) | p < 0.05 | SIRS + SEPSIS versus SIRS − SEPSIS/ NORMAL |

| MOLECULE | SEPSIS (Gram + ve) | SEPSIS (Gram − ve) | NORMAL | | |
|---|---|---|---|---|---|
| CD29 | 73% (n = 20) | 35% (n = 35) | 33% (n = 21) | p < 0.001 | SEPSIS (Gram + ve) versus SEPSIS (Gram − ve)/NORMAL |

We claim:

1. A method for determining whether a subject has a bacterial infection comprising:
   contacting detectably labeled antibodies specific for CD49e, TLR2, and TLR4 with blood leucocytes in a sample obtained from the subject;
   forming a measurable amount of CD49e-antibody complex, TLR2-antibody complex, and TLR4-antibody complex;
   identifying abnormal expression of CD49e on blood leucocytes in a sample obtained from the subject from the amount of CD49e-antibody complex; and
   identifying abnormal expression of one or both of TLR2 and TLR4 on the blood leucocytes in the sample from the amount of TLR2-antibody complex and TLR4-antibody complex, wherein abnormal expression of CD49e and of one or both of TLR2 and TLR4 is indicative of the subject having a bacterial infection.

2. The method of claim 1 wherein the sample is whole blood.

3. A method according to claim 1, wherein the leucocytes are neutrophils.

4. A method according to claim 3, wherein at least 20% of neutrophils in the sample express CD49e.

5. A method according to claim 1, wherein abnormal expression of TLR2 is identified which is indicative of a Gram positive bacterial infection.

6. A method according to claim 1, wherein abnormal expression of TLR4 is identified which is indicative of a Gram negative bacterial infection.

7. A method according to claim 1, wherein at least 10% of leucocytes in a sample express TLR2 or TLR4.

* * * * *